(12) United States Patent
Slettenmark

(10) Patent No.: US 6,266,552 B1
(45) Date of Patent: Jul. 24, 2001

(54) METHOD AND ARRANGEMENT FOR LOCATING A MEASUREMENT AND/OR TREATMENT CATHETER IN A VESSEL OR ORGAN OF A PATIENT

(75) Inventor: Bruno Slettenmark, Järfälla (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/180,337

(22) PCT Filed: May 28, 1997

(86) PCT No.: PCT/SE97/00915

§ 371 Date: Nov. 5, 1998

§ 102(e) Date: Nov. 5, 1998

(87) PCT Pub. No.: WO98/00060

PCT Pub. Date: Jan. 8, 1998

(30) Foreign Application Priority Data

Jun. 28, 1996 (SE) .................................. 9602574

(51) Int. Cl.[7] ........................................ A61B 5/05
(52) U.S. Cl. .................. 600/424; 600/425; 600/427; 600/429; 607/2; 607/6; 607/9; 607/115; 607/116; 601/1
(58) Field of Search ..................... 607/115, 122, 607/2, 6, 9, 116; 128/653; 600/407, 409, 422, 423, 437, 431, 434, 439, 424, 443, 456, 447, 459, 462, 466, 467, 481, 508, 9, 11; 601/1, 2

(56) References Cited

U.S. PATENT DOCUMENTS

| | | |
|---|---|---|
| 5,042,486 | 8/1991 | Pfeiler et al. . |
| 5,326,342 * | 7/1994 | Pflueger et al. ..................... 604/22 |
| 5,391,199 | 2/1995 | Ben-Haim . |
| 5,443,489 | 8/1995 | Ben-Haim . |
| 5,486,161 * | 1/1996 | Lax et al. ........................... 604/22 |
| 5,718,241 * | 2/1998 | Ben-Haim et al. ............... 600/515 |
| 5,827,269 * | 10/1998 | Saadat ............................... 606/28 |

FOREIGN PATENT DOCUMENTS

| | | |
|---|---|---|
| 0 485 3232 | 5/1992 | (EP) . |
| WO 93/08731 | 5/1993 | (WO) . |

* cited by examiner

*Primary Examiner*—Peter Vo
*Assistant Examiner*—Jeoyuh Lin
(74) *Attorney, Agent, or Firm*—Schiff Hardin & Waite

(57) ABSTRACT

In a method for locating a measurement and/or treatment catheter in a vessel or organ of a patient relative a fixed catheter, also positioned within the patient in the vicinity of the measurement and/or treatment catheter signals are transmitted from one of the catheters and received at the other one. The position and direction of the measurement and/or treatment catheter relative to the fixed catheter is then determined from the received signals. An arrangement for locating a measurement and/or treatment catheter, intended to be positioned in a vessel or organ of a patient, also includes a fixed catheter, also intended to be positioned within the patient in the vicinity of the measurement and/or treatment catheters. One of the catheters has a signal transmitter and the other one has a signal receiver for receiving signals from the signal transmitter. A signal processor determines from the received signals the position of the measurement and/or treatment catheter relative to the fixed catheter.

25 Claims, 4 Drawing Sheets

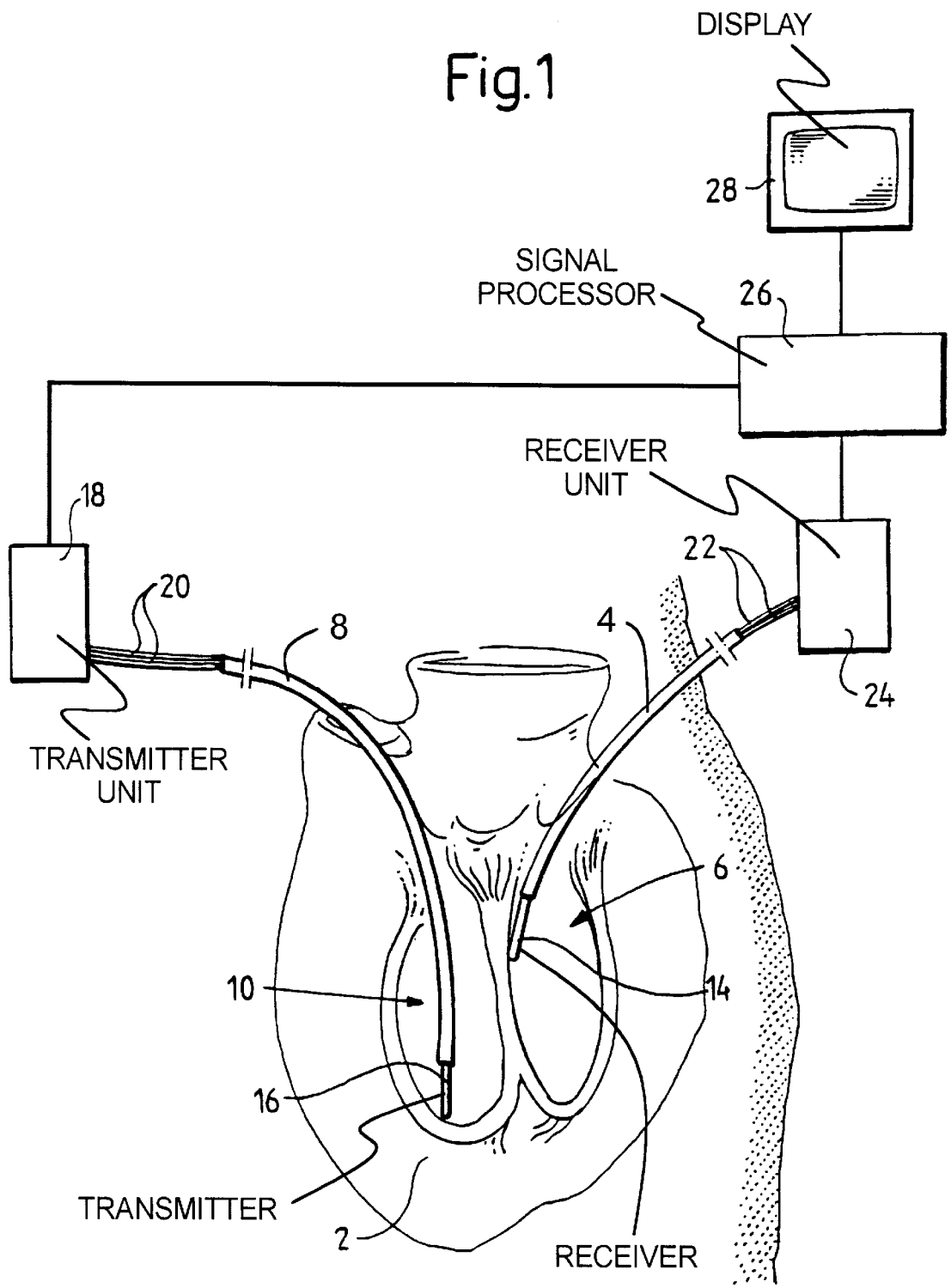

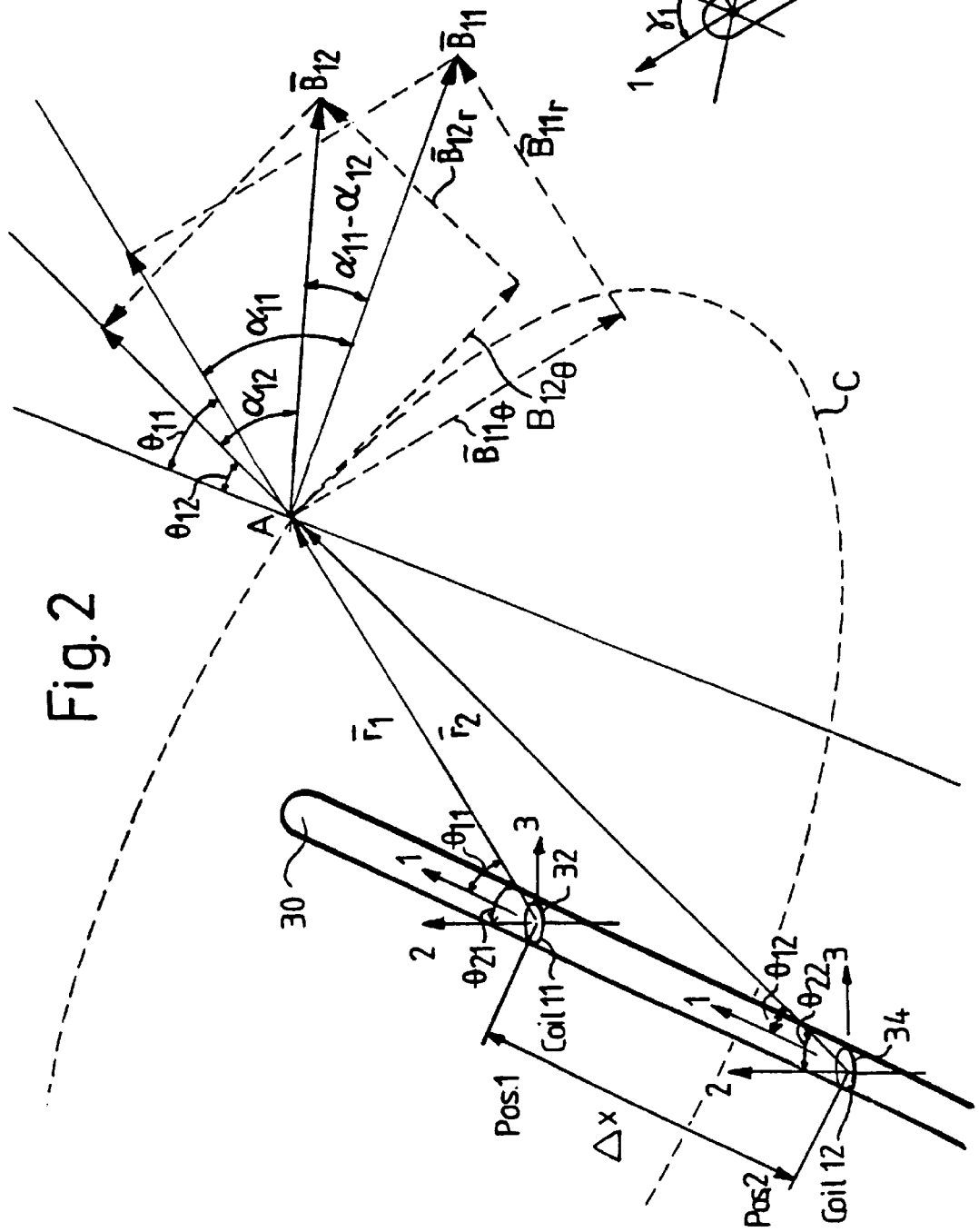

METHOD AND ARRANGEMENT FOR LOCATING A MEASUREMENT AND/OR TREATMENT CATHETER IN A VESSEL OR ORGAN OF A PATIENT

BACKGROUND OF THE INVENTION

1. Field of the Invention

The present invention is directed to a method and an arrangement for locating a measurement and/or a treatment catheter in a vessel or an organ of a patient, wherein signals are transmitted (emitted) by one of these catheters, the signals being used to locate the position of the catheter which transmitted the signals.

2. Description of the Prior Art

For many medical applications it is desirable to be able to locate a catheter in a patient, e.g. in angiographic examinations and in cardiac diagnostics and therapy.

Thus, U.S. Pat. No. 5,042,486 describes a method for real time portrayal of a catheter in a vessel, which makes use of a transmitter for electromagnetic or acoustic waves located at the tip of the catheter. These waves are received by receiving antennas attached to the exterior surface of the patient and are converted into electrical image signals. From these signals the position of the catheter relative to external antennas is determined. A disadvantage of this technique is that the patient may not flex or bend or even breathe since the external antennas will then move relative to each other and to the catheter and the information will be distorted and the results unreliable and inaccurate. In U.S. Pat. Nos. 5,391,199 and 5,443,489 apparatuses and methods for treating cardiac arrhythmias and for ablation are described. Reference catheters, having a receiving or sending antenna, are then introduced into the heart and the position of a mapping/ablating catheter relative the reference catheters is determined by use of an external transmitter or receiver. The primary image of the structure studied, e.g. the heart, upon which a catheter map is superimposed, is obtained by an appropriate method, such as by x-ray imaging. By using fixed catheters the accuracy of location is improved and the correct orientation and superposition of the vessel image and the catheter location map is facilitated. If three or more fixed reference catheters, introduced into the heart, are used, it is possible for the patient to move and breathe freely without impairing the results. It is thus possible to have the external antennas fixed relative to the room, and not necessary to have them fixed relative the patient. However, the use of external antennas for transmitting electromagnetic fields for this purpose is associated with difficulties when the patient is lying in a bed and if ultrasonic waves are used the patient should preferably be immersed in water to obtain a satisfactory signal transmission between the exterior and the interior of the patient. Thus, this technique is complicated and impractical.

SUMMARY OF THE INVENTION

An object of the present invention is to provide a technique for locating a measurement and/or treatment catheter in a vessel or organ of a patient relative a fixed catheter, serving as a reference, with which technique the above discussed disadvantages of the prior art solutions are eliminated.

The above object is achieved in accordance with the principles of the present invention in a method and an arrangement for locating a measurement and/or a treatment catheter in a vessel or an organ of a patient, wherein a fixed catheter is positioned within the patient in the vicinity of a measurement and/or treatment catheter, with signals being transmitted from one of the catheters to the other, and wherein the transmitted signals are received by the other of the catheters and the position of the measurement and/or treatment catheter relative to the fixed catheter is determined from the received signals. Thus, in the present invention the signal transmission between the measurement and/or treatment catheter and the fixed catheter takes place entirely inside the patient. Thus, the problem related to transmission of signals between the exterior and the interior of the patient are eliminated and by positioning the fixed catheter in the vicinity of the measurement and/or treatment catheter these catheters are moving together and not relative to each other. The measurement results are consequently not affected by movement or breathing of the patient. Thus with the present invention the patient is allowed to move generally freely, an important advantage to the patient.

In an embodiment of the method according to the invention the signals are transmitted from two points, separated in the longitudinal direction of the catheter. In this way also the direction of the catheter can be determined.

According to another embodiment of the method according to the invention, wherein the transmitted signals are electromagnetic signals, the sign of the phase of the received signals are determined relative to the sign of the phase of the transmitted signals in order to determine the direction of the magnetic field uniquely. In this way it is possible to determine the direction of the measurement and/or treatment catheter tip relative to the direction of the induced magnetic field $\overline{B}$ and accordingly to the direction of the fixed catheter.

According to still another embodiment of the method according to the invention the signals are formed of ultrasonic pulses, transmitted from one of the catheters and received at the other one and the position of the measurement and/or treatment catheter is determined from the flight times of the received pulses. In this way the results of the determination are independent of the amplitude of the received pulses. Further, the first signal received by the sensor in question will determine the shortest distance to the signal transmitting means and consequently reflections and scattering pose no problem.

According to another embodiment of the method according to the invention the ultrasonic pulses are transmitted from two points, separated in the longitudinal direction of one of the catheters and the pulses are received by sensors disposed on the other catheter in a triangular configuration, preferably positioned in the corners of an equilateral triangle, the transmitting points and the sensors being suitably positioned in different planes for improving the accuracy in the case of three sensors. In this way the position of the measurement and/or treatment catheter relative to the fixed catheter can be correctly determined. Of course more than three sensors can be used and the positions and number of the transmitting points and sensors can be interchanged. Theoretically it is not possible with this method, in the case of using only three sensors on the platform, to distinguish the true catheter position from its mirror positions. However, in practice this will be no problem and such a theoretical uncertainty in the obtained results can for example be eliminated by using sensors with a certain lobe directivity.

According to still another embodiment of the method according to the invention the distal tip of the measurement and/or treatment catheter is moved on a surface and the positions and directions of the tip are successively determined to map the surface. Thus, if electromagnetic signals are used the first measuring point will result in knowledge of the position and direction of the catheter tip of the measurement and/or treatment catheter relative to the fixed catheter. Since the position and direction of the fixed catheter are unknown this information does not provide much. However by moving the measurement and/or treatment catheter and repeating the measurement new positions relative to the fixed catheter are obtained which can be joined by surface elements. In this way e.g. the interior surface of a heart chamber can be mapped, including the direction of the measurement and/or treatment catheter tip, and shown as a three-dimensional image on a monitor, without knowing the starting positions of the catheters.

According to another embodiment of the method according to the invention a fluoroscopic biplane exposure or an ultrasound imaging of the catheters is performed at one stage to determine their positions relative the patient. Then it is possible to correctly orient the obtained topological map relative to the patient.

According to embodiments of the arrangement according to the invention the signal transmitter is formed by two triaxial coil systems, or a triaxial or biaxial coil system and a single coil, separated in the longitudinal direction of the catheter. It is then possible to determine the direction of the catheter relative to the other catheter having a triaxial coil system near the tip. It is important to determine the direction of the catheter tip portion, since its transmitting or receiving means are normally situated a certain distance from the catheter tip and therefore to be able to determine the exact position of the tip from the measurements the direction of the tip portion must be known. By using two triaxial coils on the transmitting catheter the arrangement will be redundant, which can be utilized to increase the precision and accuracy of the position determination.

According to another embodiment of the arrangement according to the invention the transmitter is disposed to sequentially transmit electromagnetic signals through the different coils. This is a preferred way of energizing the coils. It would be, possible to energize all the coils simultaneously with different frequencies and thereafter filtering the pickup signals with bandpass filters, however, such a procedure would be more complicated.

According to still other embodiments of the arrangement according to the invention the signal transmitter and the receiver are respectively situated in the distal tip portions of the respective catheters and respective tip portions are rigid to avoid errors in the measuring results due to flexing of the tip portions.

DESCRIPTION OF THE DRAWINGS

FIG. 1 schematically illustrates a measurement and/or treatment catheter and a fixed catheter introduced into respective chambers of a heart, in accordance with the invention.

FIG. 2 schematically illustrates the distal tip portion of the fixed catheter provided with two triaxial coils in accordance with one embodiment of the invention.

FIG. 3 illustrates the tip portion of a measurement and/or treatment catheter in accordance with the invention.

FIG. 4 shows a triaxial coil used in accordance with the present invention.

DESCRIPTION OF THE PREFERRED EMBODIMENTS

Figure 5:
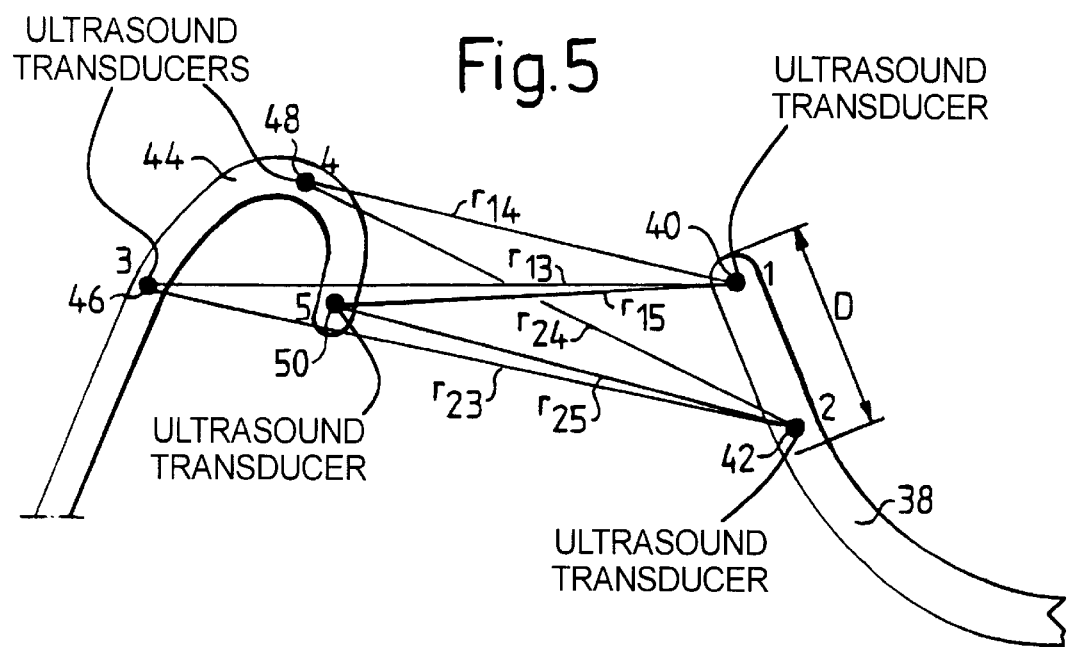
FIG. 5 schematically illustrates a further embodiment of the invention using ultrasound.

In FIG. 1 a part of a heart 2 is schematically shown with a measurement and/or treatment catheter 4 introduced into one of the heart chambers 6 and a fixed catheter 8 introduced into the other heart chamber 10. The body surface is shown at 12.

One of the catheters 4 or 8 is provided with a transmitter and the other of the catheters 4 or 8 is provided with a receiver. It is not important whether the catheter 4 is provided with a transmitter and the catheter 8 is provided with a receiver, or vice versa.

In the shown embodiment the fixed catheter 8 is connected to a transmitter unit 18 through conductors 20 for energizing the transmitter 16. The receiver means 14 of the measurement and/or treatment catheter 4 are through electrical conductors 22 extending inside the catheter 4 connected to a receiver unit 24, which is connected to a signal processor 26 for determining the position of the measurement and/or treatment catheter 4 relative the fixed catheter 8 from the received signals, as described more in detail below. The results can be shown on a display 28.

The signal processor 26 also controls the transmitter unit 18 as indicated in the Fig.

FIG. 2 illustrates the principle of one embodiment of the invention. More precisely, in the distal tip portion 30 of a fixed catheter two triaxial coils 32, 34 are mounted, separated by a certain distance $\Delta x$ in the longitudinal direction of the fixed catheter 30. The triaxial coils 32, 34 are formed as miniature crossed coil system as illustrated in FIG. 4, each coil system generating three orthogonal magnetic fields when energized. Each coil can have a diameter of 3 mm and contains 100 turns, and the distance $\Delta x$ between the two triaxial coil systems 32, 34 can typically be about 5–15 mm.

The catheter portion 30 between the coil systems 32, 34 must be rigid such that the relative positions of the coil systems remain constant. The extreme tip of the portion 30 may be flexible, precurved or maneuverable in order to facilitate introduction of the catheter to the desired position.

In the tip of the measurement and/or treatment catheter 36, see FIG. 3, there is one similar triaxial receiving or pickup coil system (not explicitly shown in FIG. 3). It is an advantage to have just one triaxial coil in one point close to the tip of the catheter 36, since a rigid tip portion is then not needed.

The coils 32, 34 in the fixed catheter 30 are preferably driven sequentially, for typically 33 $\mu s$ each, by a current of about 10 mA and a frequency of 300 kHz. With a sampling rate for the measurement cycle of 5 kHz, dynamic registration of the probe tip up to about 1 kHz can be obtained.

Since in practice 100 Hz probably is quite sufficient for accurate tracking of e.g. heart motions, the requirements on the above given parameters can be considerably less tight, giving more time for the measurements.

By a triaxial coil system in the tip of the measurement and/or treatment catheter 36 in FIG. 3 the projections of the magnetic field $\overline{B}$, $B_1$, $B_2$ and $B_3$ along the coil axis are measured in the point where this receiving or pickup coil system is situated, where $$B_1 = |\overline{B}| \cdot \cos\gamma_1$$

$$B_2 = |\overline{B}| \cdot \cos\gamma_2$$

$$B_3 = |\overline{B}| \cdot \cos\gamma_3$$

and where $$|\overline{B}| = \sqrt{B_1^2 + B_2^2 B_3^2},$$

$$\gamma_1 = \arccos\frac{B_1}{|\overline{B}|}$$

$$\gamma_2 = \arccos\frac{B_2}{|\overline{B}|}$$

$$\gamma_3 = \arccos\frac{B_3}{|\overline{B}|}$$

From the angles $\lambda_1$, $\lambda_2$, $\lambda_3$ together with the variables calculated as described in the following the direction of the measurement and/or treatment catheter tip portion relative to the fixed catheter can be derived.

If it is assumed that the receiving coil system of the measurement and/or treatment catheter 36 is positioned in point A in FIG. 2 its position can be determined as follows.

Coil 11 (the coil in position 1 with its axis parallel to the 1-axis) and coil 12 (the coil in position 2 with its axis parallel to the 1-axis) are excited sequentially. The resulting magnetic fields in point A are $$|\overline{B}_{11}| = \frac{\mu_0}{4\pi} \cdot \frac{N_1 \cdot I \cdot \pi \cdot d_1^2}{4} \cdot \frac{\sqrt{3 \cdot \cos^2\theta_{11} + 1}}{r_1^3}$$

$$\left|\overline{B}_{12}\right| = \frac{\mu_0}{4\pi} \cdot \frac{N_1 \cdot I \cdot \pi \cdot d_1^2}{4} \cdot \frac{\sqrt{3 \cdot \cos^2\theta_{12} + 1}}{r_2^3}$$

where $N_1$ denotes the number of turns of the coil, I the current to the coil and $d_2$ the diameter of the coil.

Further, the angle $\alpha_{11} - \alpha_{12}$, see FIG. 2, is given by the following relation $$\alpha_{11} - \alpha_{12} = \arctan\left[\frac{\tan\theta_{11}}{2}\right] - \arctan\left[\frac{\tan\theta_{12}}{2}\right]$$

and $$r_1^2 = (\Delta x)^2 + r_2^2 - 2 \cdot \Delta x \cdot r_2 \cdot \cos\theta_{12}$$

The angles $\alpha$ and $\theta$ appear from the figure and $r_1$ and $r_2$ denote the distances between point A and position 1 and 2 respectively.

The quantities $|\overline{B}_{11}|$, $|\overline{B}_{12}|$ and $\alpha_{11} - \alpha_{12}$ are measured with the receiving coil system and the four unknown quantities $r_1$, $r_2$, $\theta_{11}$ and $f_{12}$ can be calculated from the above four equations. The solution of these equations will consequently give the position of the point A as an undetermined point on the concentric circle C.

To determine the position of the point A along the circle C the coil 21 (the coil in position 1 with its axis parallel to the 2-axis) and the coil 22 (the coil in position 2 with its axis parallel to the 2-axis) are excited sequentially. The resulting magnetic fields in point A are then $$|\overline{B}_{21}| = \frac{\mu_0}{4\pi} \cdot \frac{N_1 \cdot I \cdot \pi \cdot d_1^2}{4} \cdot \frac{\sqrt{3 \cdot \cos^2\theta_{21} + 1}}{r_1^3}$$

$$\left|\overline{B}_{22}\right| = \frac{\mu_0}{4\pi} \cdot \frac{N_1 \cdot I \cdot \pi \cdot d_1^2}{4} \cdot \frac{\sqrt{3 \cdot \cos^2\theta_{22} + 1}}{r_2^3}$$

From these equations $\theta_{21}$ and $\theta_{22}$ are calculated, since $|\overline{B}_{21}|$ and $|\overline{B}_{22}|$ are measured and $r_1$ and $r_2$ have been determined above.

Further, the angle between $$|\overline{B}_{21}| \text{ and the 2-axis} = \theta_{21} + \arctan\left(\tan\frac{\theta_{21}}{2}\right)$$

the angle between $$|\overline{B}_{22}| \text{ and the 2-axis} = \theta_{22} + \arctan\left(\tan\frac{\theta_{22}}{2}\right)$$

are calculated and thus the position of A is determined.

In fact the coil 22 and the corresponding measurements are redundant but it is desirable to use it to increase the accuracy of the position determination. In the same way it can be desirable to make corresponding measurements with the additional coils 31 (the coil in position 1 with its axis parallel to the 3-axis) and coil 32 the coil in position 2 with its axis parallel to the 3-axis) to further improve the accuracy.

If the sign of the phase of the signal induced in the receiving coil system is measured relative to the phase of the excited transmitting coils the direction of the catheter relative to the magnetic field $\overline{B}$ and accordingly to the fixed catheter is uniquely determined.

A minimum requirement for determining the desired position and direction of the measurement and/or treatment catheter is realized by a configuration using three coils on the fixed catheter. One preferred embodiment includes the use of one crossed biaxial coil system and a single coil separated along the catheter as described above. However, other configurations are possible, e.g. a single orthogonal triaxial coil system or three single coils arranged in a suitable configuration. By using two triaxial coil system as described above the accuracy of the determination can be further improved.

With the present invention it is possible not only to determine position and direction of the catheter but also velocity and amplitude of the catheter tip. If the movement of the catheter tip shall be determined with a frequency limit of 1 kHz it will be necessary to sample with a frequency exceeding 2 kHz, e.g. 5 kHz. If at least 10 cycles are needed for forming average values and if 3–6 transmitting coils are used for sequential excitation a signal frequency of 150–300 kHz is needed.

Above only sequential excitation of the coils has been described. It is, however, also possible to excite all coils simultaneously with different frequencies and then filtering the received or pick-up signals with bandpass filters. Such a solution would, however, be more complicated.

The invention can be used to e.g. map the interior surface of a heart chamber in the following way as indicated above.

The fixed and the measurement and/or treatment catheters are both positioned somewhere inside the heart, c.f. FIG. 1. No fluoroscopic investigation is performed and the position and direction of the catheters are unknown.

The distal tip of the measurement and/or treatment catheter is moved on a surface inside the heart and the positions of the tip are successively determined to map the surface. Thus, when measuring the first point the distance and orientation of the measurement and/or treatment catheter relative to the unknown position and orientation of the fixed catheter is obtained. By moving the measurement and/or treatment catheter and repeating the measurements new relative positions are obtained which can be joined by surface elements. In this way the interior surface of the heart chamber in which the measurement and/or treatment catheter is positioned is mapped and can be shown together with the direction of the measurement and/or treatment catheter tip on a monitor as a simulated three-dimensional representation without knowing the starting positions of the catheters.

If it is desirable, however, to orient this topological map correctly relative to the patient it will be necessary to make one fluoroscopic biplane exposure and relate the observed positions of the two catheter tips to the mapped data.

Pairs of measurement and/or treatment and fixed catheters should preferably be calibrated together at the manufacture since a perfect orthogonality between the coils is in practice difficult to obtain. The calibration is preferably performed in an isotonic salt solution if the frequency used makes this necessary. One way of performing the calibration would be to let a robot move the measurement and/or treatment catheter relative to the fixed catheter in a number of positions and angles and deliver all the measured and calculated corrections on a diskette which is supplied with the catheter set to be inserted in the workstation at the clinic. A simple last calibration for the current amplitude to the transmitting coils can be made at the clinic, putting the catheters in a simple fixture.

If a fast real time registration of a rapidly moving catheter tip is needed the solving of the nonlinear equation system described above might be too time consuming for the workstation. It may then be necessary to have the equation system solved in advance for a large number of positions and stored in a look-up table. In most cases, storing the array of measured variables in a memory, will allow enough time for the calculations to be performed during the time it takes to move the catheter tip from one sampling position to the next one.

In the above embodiments electromagnetic signals have been used. In FIG. 5 an alternative embodiment is shown using ultrasonic signals.

In the embodiment of FIG. 5, measurement and/or treatment catheter 38 is then provided with a transmitter in the form of two ultrasound transducers 40, 42 in positions 1 and 2. A fixed catheter 44 is provided with at least three sensors 46, 48, 50 in the form of three ultrasound transducers in the positions 3, 4 and 5 in the tip portion. The tip portion of the fixed catheter 44 must, when in position, be curved in a controlled and stable manner to serve as a triangular platform for the transducers 46, 48 and 50 in the case of three transducers. The transducers 46, 48, So must not be in line and the receiving transducers 46, 48, 50 and the transmitting transducer 40, 42 are preferably situated in different planes in order to improve the position determination accuracy.

Figure 6:
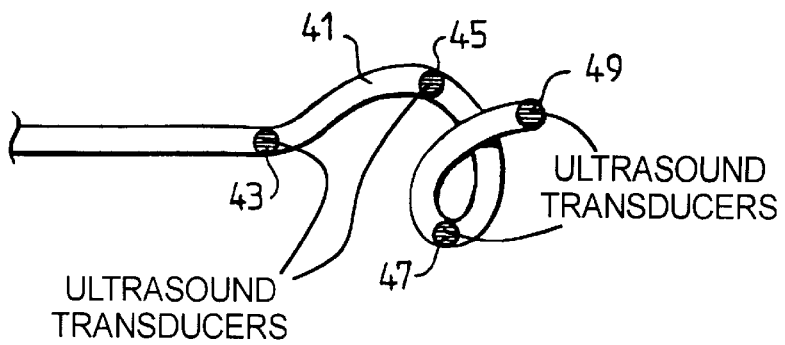
FIG. 6 shows a helical, three-dimensional ultrasound transducer arrangement used in accordance with the invention.

Another preferred embodiment of the arrangement according to the invention can be realized by e.g. a double-curved, helical tip portion, see FIG. 6, which shows a helical three-dimensional ultrasound transducer platform 41, formed on a catheter distal end and having more than three transducers 43, 45, 47, 49 carried on the platform 41. The catheter distal end portion can be formed of e.g. a memory alloy for forming the catheter distal end portion to a platform 41 of desired shape after introduction into the vessel or organ in question.

Also the tip portion, denoted by D in FIG. 5, must be rigid such that the relative position of the transducers 40 and 42 is not changed. If it is not of interest to be able to determine the direction of the tip portion of the catheter 38 only one transducer of this catheter, e.g. 40 is needed and the tip portion may be completely flexible, which is an advantage.

Short ultrasound pulses are segmentally from the transducers 40, 42 and the flight times of these pulses to the transducers 46, 48 and 50 are measured, these transit times being a direct measure of the distance to the transmitting and receiving transducers. To improve the accuracy of the measurement more than three transducers can be used on the platform.

The frequency of the ultrasound signals is preferably in the range of 10–30 MHz.

If five of the six distances $r_{13}$, $r_{14}$, $r_{15}$, $r_{23}$, $r_{24}$ and $r_{25}$ are determined the position and the direction of the measurement and/or treatment catheter 38 is determined.

The position is, in the case where only three transducers are utilized on the platform, or more than three sensors positioned in the same plane, not uniquely determined since also the mirrored position is possible. In practice this will, however, pose no problem, as discussed above.

Since the first signal received by the sensors 46, 48, 50 will determine the shortest distance from the transmitting transducers 40, 42, reflections and scattering will give rise to no problems either.

An advantageous feature of this method is the fact that the measurements are independent of the amplitude of the ultrasonic signals.

Instead of transmitting short pulses with constant frequency from the transducers 40, 42 they can be excited to transmit a modulated pulse train with successively changing frequency, so called chirped pulse train, or other kinds of modulation according to previously known techniques.

Figure 7:
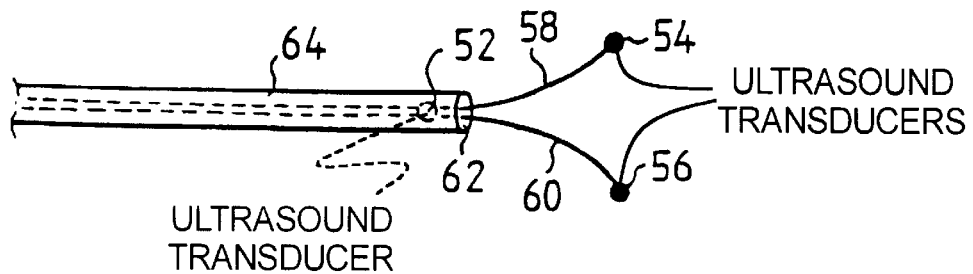
FIGS. 7–9 respectively show further embodiments of ultrasound transducer arrangements usable in accordance with the invention.
Figure 8:
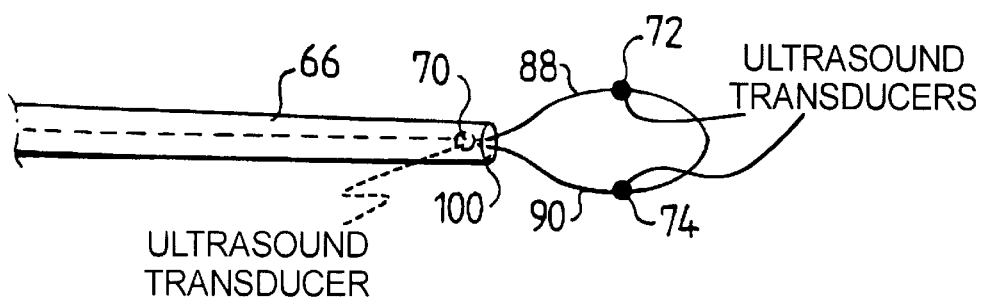
Figure 9:
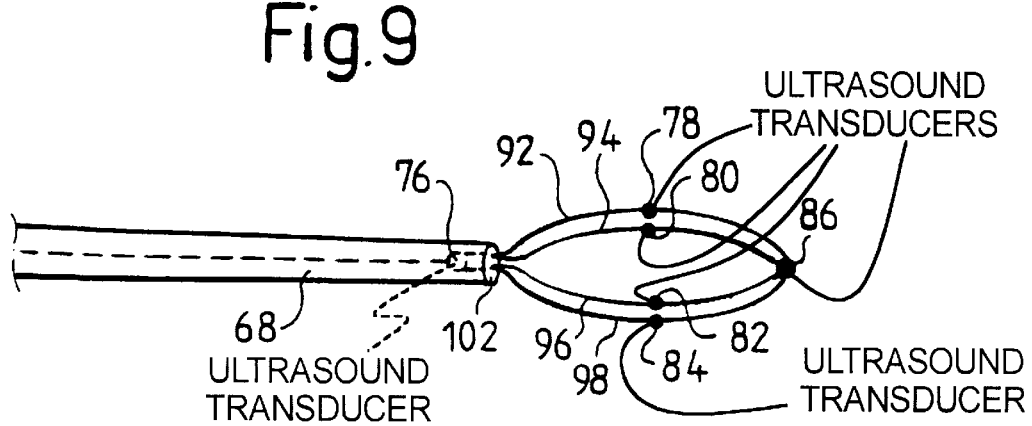

FIG. 7–9 show alternative embodiments of the arrangement for the transducers. In the embodiment according to FIG. 7 the transducers 52, 54 and 56 are mounted on two wires 58, 60 which can be pushed out of the mouth 62 of the catheter 64 after insertion of the catheter 64 into the body vessel or organ in question.

FIGS. 8 and 9 show a loop and a basket catheter 66 and 68 respectively with transducers 70, 72, 74 and 76, 78, 80, 82, 84, 86 mounted on wires 88, 90 and 92, 94, 96, 98 respectively forming a loop and a basket which can be retracted into the catheters 66, 68 for insertion of the catheters and pushed out of the catheter mouths 100, 102 when the catheters 66, 68 have reached their positions. The wires 92, 94, 96, 98 are arranged about 90 degrees apart, so that the sensors 76, 78, 80, 82, 84, 86 span a three-dimensional volume.

The wires 58, 60, 88, 90, 92, 94, 96 and 98 can be precurved or alternatively formed of e.g. NiTi memory alloys and provided with suitable heating means for expanding the wires to desired shapes forming the arrangement platform for the transducers 52, 54, 56, 70, 72, 74, 76, 78, 80, 82, 84.

When a platform has been expanded or brought to a desired shape, the relative positions of all the transducers 46, 48, 50 and 52, 54, 56 and 70, 72, 74 and 76, 78, 80, 82, 84 respectively can, if necessary, be determined by measuring the distances from each transducer to all the other transducers on the arrangement in the way described above. It is then possible to therefrom calculate the exact shape of the platform which is a necessary basis for determining the position of the other catheter. In this way it is also possible to verify that the shape of the arrangement is not changed during the measurement.

As still another alternative static magnetic fields can be used for determining the catheter position according to the invention. The transmitter of the catheters then are formed by coils fed with a constant electric current or permanent magnets and the receiver are formed by e.g. Hall-elements or similar devices sensing magnetic DC fields from which the relative position can be determined. In order to compensate for the earth's magnetic field and possible other disturbing magnetic fields the current to the transmitter coils can be switched on and off to determine and correct for the interfering magnetic fields from the difference thus obtained.

It should be observed that throughout the description above of the invention the locations of the transmitters and receivers, respectively, both for embodiments for electromagnetic and for ultrasonic signals, can be interchanged, i.e. transmitters can be mounted as well on the fixed reference catheter as on the measurement and treatment catheters and vice versa for the receivers means.

Although modifications and changes may be suggested by those skilled in the art, it is the intention of the inventor to embody within the patent warranted hereon all changes and modifications as reasonably and properly come within the scope of his contribution to the art.

What is claimed is:

1. A method for locating a catheter in a patient comprising the steps of:

intracorporeally placing a movable catheter in a patient, said catheter being selected from the group consisting of measurement catheters and treatment catheters;

simultaneously intracorporeally placing a fixed catheter in a patient in a vicinity of said catheter;

intracorporeally transmitting electromagnetic signals between said fixed catheter and said movable catheter, with one of said fixed catheter and said catheter serving as a signal transmitter and the other of said fixed catheter said movable catheter and serving as a signal receiver, said signal receiver receiving received electromagnetic signals; and processing said received electromagnetic signals to identify an intracorporeal position of said movable catheter relative to an intracorporeal position of said fixed catheter.

2. A method as claimed in claim 1 wherein said signal transmitter has a longitudinal direction, and comprising the step of transmitting said electromagnetic signals from said signal transmitter at two points spaced from each other along said longitudinal direction.

3. A method as claimed in claim 1 wherein said signal receiver has a longitudinal direction, and comprising the step of receiving said received electromagnetic signals at two points separated along said longitudinal direction.

4. A method as claimed in claim 1 wherein said signal transmitter has a longitudinal direction and wherein said signal receiver has a longitudinal direction, and said method comprising the steps of transmitting said electromagnetic signals from two points separated along said longitudinal direction of said signal transmitter, and receiving said received electromagnetic signals at two points separated along the longitudinal direction of said signal receiver.

5. A method as claimed in claim 1 comprising the step of moving said movable catheter in an intracorporeal direction in said patient.

6. A method as claimed in claim 5 wherein the step of transmitting said electromagnetic signals comprises transmitting electromagnetic signals each having a phase with a sign, and wherein said received signals each have a phase with a sign, and wherein the step of processing said received electromagnetic signals comprises identifying the sign of the phase of the received electromagnetic signals relative to the sign of the phase of the transmitted electromagnetic signals to identify said intracorporeal direction of said catheter.

7. A method as claimed in claim 1 wherein said movable catheter has a distal tip, and wherein said method comprises the additional step of moving said distal tip intracorporeally in successive directions to assume successive positions along an intracorporeal path, and wherein the step of processing said received electromagnetic signals comprises processing said received electromagnetic signals to identify said successive positions and directions of said distal tip to identify said path of said distal tip.

8. A method as claimed in claim 7 wherein the step of moving said distal tip comprises moving said distal tip on an intracorporeal surface, and wherein the step of processing said received electromagnetic signals comprises mapping said surface using said successive positions and successive directions of said distal tip.

9. An apparatus for locating a catheter in a patient, comprising:

a fixed catheter adapted to be disposed at a fixed intracorporeal position in a patient;

a movable catheter, selected from the group consisting of measurement catheters and treatment catheters, adapted to be movably intracorporeally positioned in a patient;

a signal transmitter carried by one of said fixed catheter and said movable catheter for intracorporeally transmitting signals;

a receiver carried by the other of said fixed catheter and said movable catheter for intracorporeally receiving said signals from said transmitter as received electromagnetic signals; and a signal processor supplied with said received signals for analyzing said received electromagnetic signals and identifying an intracorporeal position of said movable catheter relative to said intracorporeal position of said fixed catheter.

10. An apparatus as claimed in claim 9 wherein said transmitter is carried on said fixed catheter and wherein said receiver is carried on said movable catheter.

11. An apparatus as claimed in claim 9 wherein said movable catheter is movable along an intracorporeal direction in said patient.

12. An apparatus as claimed in claim 11 wherein said transmitter comprises at least one triaxial transmission coil system which emits said electromagnetic signals, with a phase having a sign, and wherein said receiver comprises at least one triaxial receiver coil system which receives said received electromagnetic signals, with a phase having a sign, and wherein said signal processor analyzes said received electromagnetic signals to identify the sign of the phase thereof relative to the sign of the phase of the transmitted electromagnetic signals to identify said intracorporeal direction of said movable catheter.

13. An apparatus as claimed in claim 9 wherein said transmitter comprises at least one crossed biaxial transmitting coil and a single transmitting coil, separated from said biaxial transmitting coil.

14. An apparatus as claimed in claim 9 wherein said receiver comprises at least one crossed biaxial receiving coil and a single receiving coil, separated from said biaxial receiving coil.

15. An apparatus as claimed in claim 9 wherein said transmitter comprises at least three single coils disposed in a selected configuration at said one of said fixed catheter and said movable catheter.

16. An apparatus as claimed in claim 9 wherein said receiver comprises at least three single coils disposed in a selected configuration at said other of said fixed catheter and said movable catheter.

17. An apparatus as claimed in claim 9 wherein said one of said fixed catheter and said movable catheter has a longitudinal axis, and wherein said transmitter comprises two triaxial transmitting coil systems, separated along said longitudinal axis of said one of said fixed catheter and said movable catheter.

18. An apparatus as claimed in claim 9 wherein said other of said fixed catheter and said movable catheter has a longitudinal axis, and wherein said receiver comprises two triaxial reception coil systems, separated along said longitudinal axis of said other of said fixed catheter and said movable catheter.

19. An apparatus as claimed in claim 9 wherein said one of said fixed catheter and said movable catheter has a longitudinal axis, and wherein said transmitter comprises a coil system, selected from the group consisting of biaxial coil systems and triaxial coil systems, and a single coil, separated from said coil system along said longitudinal axis of said one of said fixed catheter and said movable catheter.

20. An apparatus as claimed in claim 9 wherein said other of said fixed catheter and said movable catheter has a longitudinal axis, and wherein said receiver comprises a coil system selected from the group consisting of biaxial coil systems and triaxial coil systems, and a single coil separated from said coil system along said longitudinal axis of said other of said fixed catheter and said movable catheter.

21. An apparatus as claimed in claim 9 wherein said transmitter comprises a plurality of different transmitting coils and transmits said signals sequentially from said different transmitting coils.

22. An apparatus as claimed in claim 9 wherein said transmitter comprises a plurality of different transmitting coils and transmits said signals continuously from said different transmitting coils.

23. An apparatus as claimed in claim 9 wherein said one of said fixed catheter and said movable catheter has a first distal tip and wherein said transmitter is disposed at said first distal tip, and wherein said other of said fixed catheter and said movable catheter has a second distal tip and wherein said receiver is disposed at said second distal tip.

24. An apparatus as claimed in claim 23 wherein each of said first distal tip and said second distal tip is rigid.

25. An apparatus as claimed in claim 9 further comprising means for synchronizing said signal processor with an ECG signal obtained from a patient to compensate for physiological caused movement of said fixed catheter and said movable catheter in a patient.

\* \* \* \* \*